United States Patent [19]

Mease et al.

[11] Patent Number: 5,428,156
[45] Date of Patent: Jun. 27, 1995

[54] SYNTHESIS OF MACROCYCLIC POLYAMINOCARBOXYLATES AND THEIR USE FOR PREPARING STABLE RADIOMETAL ANTIBODY IMMUNOCONJUGATES FOR THERAPY, SPECT AND PET IMAGING

[75] Inventors: Ronnie C. Mease, Fairfax, Va.; Leonard F. Mausner, Stony Brook; Suresh C. Srivastava, Setauket, both of N.Y.

[73] Assignee: Associated Universities, Inc., Washington, D.C.

[21] Appl. No.: 42,249

[22] Filed: Apr. 2, 1993

[51] Int. Cl.[6] .......................................... C07D 257/00
[52] U.S. Cl. .................................................. 540/474
[58] Field of Search .................. 540/474; 534/10, 14, 534/15, 16; 548/523, 524

[56] References Cited

U.S. PATENT DOCUMENTS

| | | | |
|---|---|---|---|
| 2,407,645 | 9/1946 | Bersworth | 260/534 |
| 4,168,265 | 9/1979 | Tabushi et al. | 260/239 |
| 4,602,106 | 7/1986 | Blanc | 562/444 |
| 4,639,365 | 1/1987 | Sherry | 424/9 |
| 4,678,667 | 7/1987 | Meares et al. | 424/85 |
| 4,880,008 | 11/1989 | Lauffer | 128/654 |
| 4,885,153 | 12/1989 | Wilbur et al. | 424/1.1 |
| 4,889,931 | 12/1989 | Rocklage et al. | 540/465 |
| 4,923,985 | 5/1990 | Gansow et al. | 540/474 |
| 5,021,571 | 6/1991 | Mease et al. | 544/166 |
| 5,049,667 | 9/1991 | Schaefer et al. | 540/474 |
| 5,053,503 | 10/1991 | Dean et al. | 540/474 |
| 5,082,599 | 1/1992 | Oftring et al. | 252/546 |
| 5,089,663 | 2/1992 | Mease et al. | 562/507 |
| 5,101,041 | 3/1992 | Troutner et al. | 548/518 |
| 5,132,409 | 7/1992 | Felder et al. | 534/10 |
| 5,316,757 | 5/1994 | Sherry et al. | 424/9 |

OTHER PUBLICATIONS

Solomons, *Organic Chemistry*, 4th Ed., 1986, p. 849.
Cox et al., *J. Chem. Soc., Chem. Comm.*, 1989, pp. 797–798.
Wu et al., Nucl. Med. Biol. vol. 19(2), 1992, pp. 239–244.
The Merke Index, 11th Ed., 1989, p. 63.
Marsden, *Solvents Guide*, 1963, pp. 9–15.
J. F. Desreux, Inorg. Chem. 19:1319–1324 (1980).
R. G. Buckley and F. Searle, FEBS Letters 166: 202–204 (1984).
M. K. Moi, et al., Analytical Biochemistry 148:249–253 (1986).
M. K. Moi and C. F. Meares, J. Am. Chem. Soc. 110:6266–6267 (1988).
M. Magerstadt, et al., Magnetic Resonance in Medcine 3:808–812 (1986).
J. P. L. Cox et al., J. Chem. Soc. Chem. Commun. 1989: 797–798 (1989).
C. F. Meares, et al. Br. J. Cancer 62(Suppl.X):21–26 (1990).
P. F. Sieving, et al., Bioconjugate Chem. 1:65–71 (1990).
M. J. McCall, et al., Bioconjugate Chem. 1:222–226 (1990).
S. V. Deshpande, et al., J. Nucl. Med. 31:473–479 (1990).
O. A. Gansow, Nucl. Med. Biol. 18:369–381 (1991).
S. J. Kline, Bioconjugate Chem. 2:26–31 (1991).
D. D. Dischino, et al., Inorg. Chem. 30: 1265–1269 (1991).
C. Wu, et al., Nucl. Med. Biol. 19:239–244 (1992).
S. C. Srivastava et al., IXth International Symposium on Radiopharmaceutical Chemistry, Paris, France, Apr. 6–10, 1992.
Mease, et al., J. Nucl. Med. 33:942 (May, 1992).
S. C. Srivastava, et al., J. Nucl. Med. 33:1030 (May, 1992).

*Primary Examiner*—Gary Geist
*Assistant Examiner*—Lara E. Chapman
*Attorney, Agent, or Firm*—Margaret C. Bogosian

[57] ABSTRACT

A simple method for the synthesis of 1,4,7,10-tetraazacyclododecane N,N'N",N'''-tetraacetic acid and 1,4,8,11-tetraazacyclotetradecane N,N',N",N'''-tetraacetic acid involves cyanomethylating 1,4,7,10-tetraazacyclododecane or 1,4,8,11-tetraazacyclotetradecane to form a tetranitrile and hydrolyzing the tetranitrile. These macrocyclic compounds are functionalized through one of the carboxylates and then conjugated to various biological molecules including monoclonal antibodies. The resulting conjugated molecules are labeled with radiometals for SPECT and PET imaging and for radiotherapy.

2 Claims, 2 Drawing Sheets

SYNTHESIS OF MACROCYCLIC POLYAMINOCARBOXYLATES AND THEIR USE FOR PREPARING STABLE RADIOMETAL ANTIBODY IMMUNOCONJUGATES FOR THERAPY, SPECT AND PET IMAGING

This invention was made with government support under contract number DE-AC02-76CH00016 between the U.S. Department of Energy and Associated Universities and NIH Grant CA-51958. The government has certain rights in the invention.

BACKGROUND OF THE INVENTION

1. Field of the Invention

The invention relates to the synthesis of macrocyclic polyaminocarboxylate chelating agents which can be used for the stable attachment of radiometals to biological molecules such as proteins and antibodies. The conjugated chelates can be used for diagnostic and therapeutic applications.

2. Description of the Related Art

Macrocyclic polyaminocarboxylates such as 1,4,7,10-tetraazacyclododecane N,N',N'',N'''-tetraacetic acid (DOTA) and 1,4,8,11-tetraazacyclotetradecane N,N'N'',N'''-tetraacetic acid (TETA) are known to bind metals very tightly.

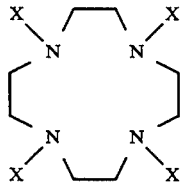

1  X = H, 1,4,7,10-tetraazacyclododecane
   X = $CH_2CO_2H$, DOTA

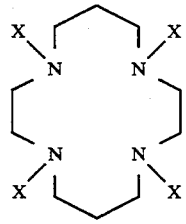

2  X = H, 1,4,8,11-tetraazacyclotetradecane
   X = $CH_2CO_2H$, TETA

DOTA and TETA were first prepared by J.F. Desreux (Inorg. Chem. 19:1319, 1980), by alkylation of 1,4,7,10-tetraazacyclododecane 1 and 1,4,8,11-tetraazacyclotetradecane 2 respectively with chloroacetic acid in base followed by acidification which sometimes precipitates the crude product. The crude product was further purified on cation exchange resin.

U.S. Pat. Nos. 5,132,409, 5,049,667, 4,923,985, 4,678,667 and 4,639,365 describe the synthesis of derivatives of 1,4,7,10-tetraazacyclododecane 1 and 1,4,8,11-tetraazacyclotetradecane 2 which are converted to the corresponding derivatives of DOTA and TETA using haloacetic acid with methods similar to that of Desreux, Id.

The ability of DOTA and TETA to tightly bind metals is advantageously used in contrast agents for magnetic resonance imaging, e.g. gadolinium-DOTA described by Magerstadt et al., Mag. Res. in Med. 3:808–812 (1986), and for the formation of stable radiometal labeled antibodies for diagnosis and/or therapy as described by Meares et al., Br. J. Cancer 62:21–26 (1990). For chemical attachment to antibody, DOTA and TETA must be suitably functionalized. In order to attach DOTA and TETA to antibodies these ligands must be derivatized with a group which can react with a group on the antibody such as an amine or sulfhydryl group. Several lengthy synthetic routes have been proposed to functionalize the carbon backbone of DOTA and TETA.

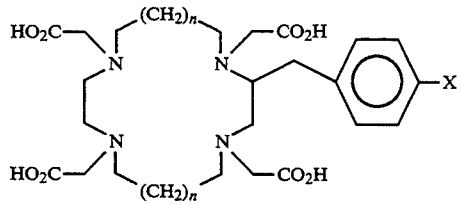

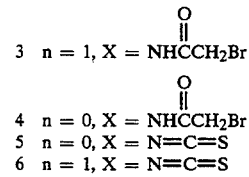

3  n = 1, X = $NHCCH_2Br$ (with C=O)
4  n = 0, X = $NHCCH_2Br$ (with C=O)
5  n = 0, X = N=C=S
6  n = 1, X = N=C=S A para-bromoacetamidobenzyl derivative of TETA 3 was prepared by M. K. Moi et al., Anal,. Biochem. 148: 249–253 (1985) and U.S. Pat. No. 4,678,667 utilizing a low yield (about 12%) cyclization reaction. The para-bromoacetamidobenzyl derivative of DOTA 4 was also prepared by M. K. Moi et al., J. Am. Chem. Soc. 110: 6266–6267 (1988) and U.S. Pat. No. 4,678,667 using a higher yield intramolecular cyclization reaction. Compounds 3 and 4 were conjugated to antibodies via 2-iminothiolane as described by M. J. McCall et al., Bioconjugate Chem. 1: 222–226 (1990). Para-isothiocyanato-benzyl-DOTA and -TETA derivatives, compounds 5 and 6 were prepared by a different route whose key cyclization step, utilized two acylation reactions under high dilution conditions as described by O. A. Gansow, Nucl. Med. Biol. 18: 369–381 (1991) and U.S. Pat. No. 4,923,985. Compounds 5 and 6 did not require treatment of the antibody with 2-iminothiolane for conjugation.

Another functionalized DOTA, 1-n-butylamino-DOTA, was prepared by Cox et al., J. Chem. Soc. Chem. Commun. 1989: 797–798 (1989). The key step in this route was a Richman Atkins cyclization. This compound was then further functionalized by reacting with the p-nitrophenyl ester of 2-vinyl-6-(4'-carboxy-3'-oxabutyl)pyridine to give 7 which could then be attached to antibodies using 2-iminothiolane.

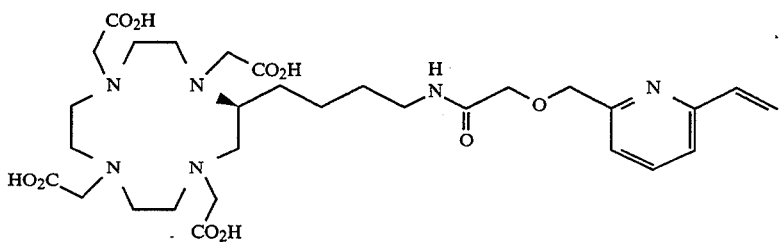

7

All the methods listed above for the preparation of functionalized DOTA or TETA require long multi-step syntheses containing difficult cyclization steps. Others have investigated shorter routes which start with the commercial macrocycles 1,4,7,10-tetraazadodecane 1 or 1,4,8,11-tetraazacyclotetradecane 2. For example, a route to 8 which leaves one nitrogen available for further functionalization has been described by Dischino et al., Inorg. Chem. 30: 1265–1269 (1991). The Dischino et al. method is similar to that of Desreux, Inorg. Chem. 19: 1319 (1980) discussed above, involves the alkylation of commercially available 1,4,7,10-tetraazacyclododecane 1 with chloroacetic acid and requires anion exchange purification. The synthesis of 9 which is DOTA functionalized on a carbon alpha to one of the carboxylates is described by Kline et al., Bioconj. Chem. 2: 26–31 (1991). The key step in the Kline et al. synthesis is the alkylation of 1 to give 10. The non-alkylated amine is then further functionalized to give 9.

A simpler method of functionalizing DOTA which sacrifices one of the carboxylates is to form the mixed anhydride with isobutylchloroformate to give 11. Poly-lysine-DOTA (Sieving et al., Bioconj. Chem.. 1:65, 1990) and biotin-DOTA (Wu et al., Nucl. Med. Biol. 19:239, 1992) have been prepared by this method. A drawback of this method is that mixed anhydrides are very prone to hydrolysis and therefore these preparations cannot be stored for any length of time.

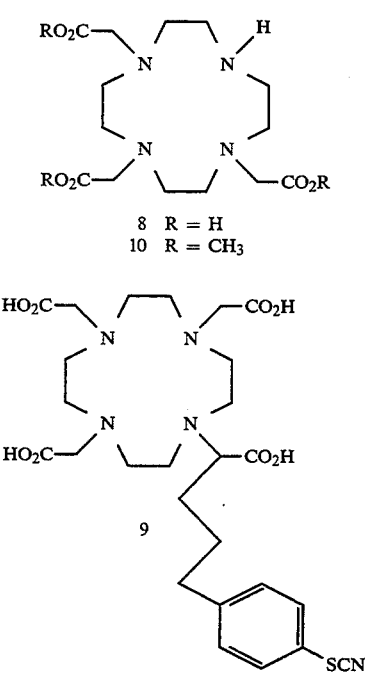

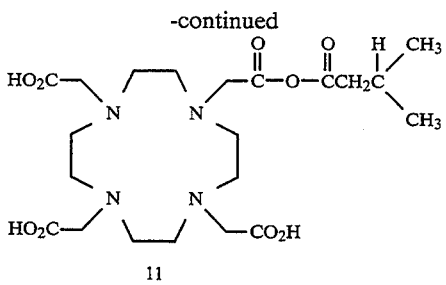

11

Previously described methods for the synthesis of DOTA and TETA have the disadvantages of requiring the use of haloacetic acid and require purification of the product by ion exchange. Other methods involve lengthy multi-step syntheses and difficult cyclization reactions and some yield unstable mixed anhydride product. Therefore, it would be highly desirable to provide a simple, high yield synthetic method for DOTA and TETA which can be coupled with a simple but effective functionalization reaction.

Furthermore, conjugation of DOTA and TETA chelates to antibody may be adversely affected by crosslinking. Crosslinking occurs when two or more active esters or mixed anhydrides are formed on each ligand and each active ester group/mixed anhydride reacts with a different antibody, thereby crosslinking the two antibodies. Crosslinking of antibodies produces dimers and oligomers which increases the molecular weight of the conjugate and results in an increase in non-target liver uptake of the labeled preparation. This can occur with the active ester or mixed anhydride methods since both are formed from the tetraacids. The key in these is to limit the formation of ester or mixed anhydride to one group per molecule. This is usually done by using excess DOTA or TETA when making the active ester or mixed anhydride. But since mixed anhydrides are readily hydrolyzed (split by the addition of water), and since a biological compound being conjugated is usually in water, water competes with the group being conjugated. Therefore, anhydrides are not very efficient. This disadvantage is shared by some of the prior art conjugation methods described above and also by the DTPA dianhydride method. Therefore it would be desirable to synthesize DOTA and TETA derivatized in a manner which allows chemical attachment to antibody with no cross-linking and gives immunoconjugates that have good serum stability and that produce good tissue distribution in vivo.

SUMMARY OF THE INVENTION

Accordingly, the invention provides a method for the synthesis of 1,4,7,10-tetraazacyclododecane N,N',N'',N'''-tetraacetic acid (DOTA) and 1,4,8,11-tetraazacyclotetradecane N,N',N'',N'''-tetraacetic acid (TETA) (Formula I). For this purpose 1,4,7,10-tetraazacyclododecane and 1,4,8,11-tetraazacyclotetradecane (Formula II) are provided and cyanomethylated using acid, formaldehyde, and cyanide compound yielding a tetranitrile (Formula III) which precipitates upon the addition of base.. The tetranitrile (Formula III) is hydrolyzed followed by acidification, evaporation to dryness, reconstitution and precipitation to give DOTA or TETA.

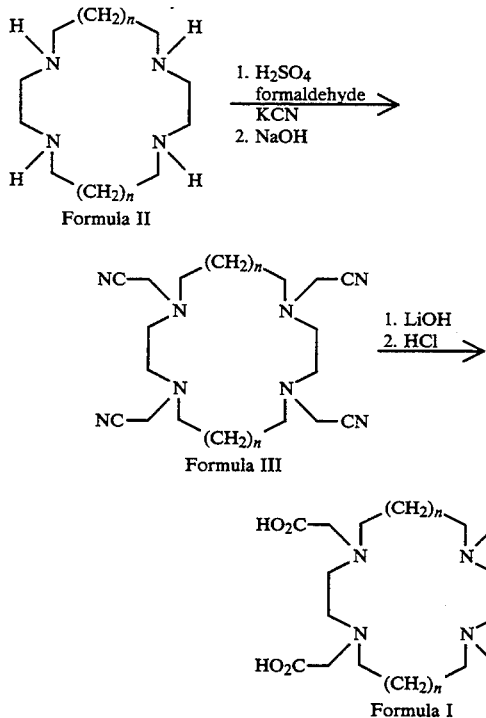

Formula II

Formula III

Formula I

The advantages of this route of DOTA/TETA synthesis over existing routes are 1) its simplicity; 2) reactions proceed in high yield; 3) no purification by chromatography is needed.

The DOTA or TETA thus synthesized may be functionalized by the reaction of excess DOTA/TETA with N-hydroxysuccinimide and dicyclohexyl carbodiimide so that statistically one carboxy group is derivatized as an activated ester.

The functionalized DOTA or TETA may be conjugated to antibody by attachment through the activated ester site on the functionalized DOTA or TETA.

When chelated with radiometals, the compounds may be used for therapeutic applications and diagnostic applications such as SPECT and PET imaging. Radioimmunoconjugates of the present invention show good tumor uptake with lower non-specific uptake of radioactivity in bone, liver, kidney and other normal tissues.

DETAILED DESCRIPTION OF THE INVENTION

Figure 1A:
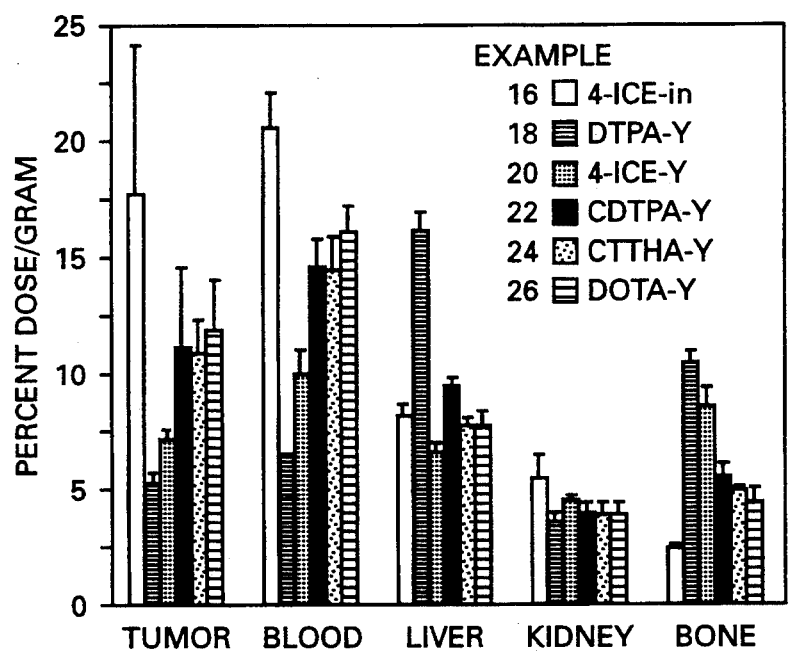
FIGS. 1a and 1b are bar graphs illustrating tissue distribution of immunoconjugates in vivo.

The invention is a method for a general synthesis of macrocyclic polyaminocarboxylate metal chelating agents for the stable attachment of radiometals to biological molecules including proteins and antibodies for diagnostic as well as therapeutic applications. The chelating agents prepared by this method include high yields of 1,4,7,10-tetraazacyclododecane N,N',N'',N'''-tetraacetic acid (DOTA) and 1,4,8,11-tetraazacyclotetradecane N,N',N'',N'''-tetraacetic acid (TETA)

These chelating agents may be synthesized, derivatized, conjugated to antibodies and/or used to chelate radiometals.

The synthesis is illustrated in Scheme 1:

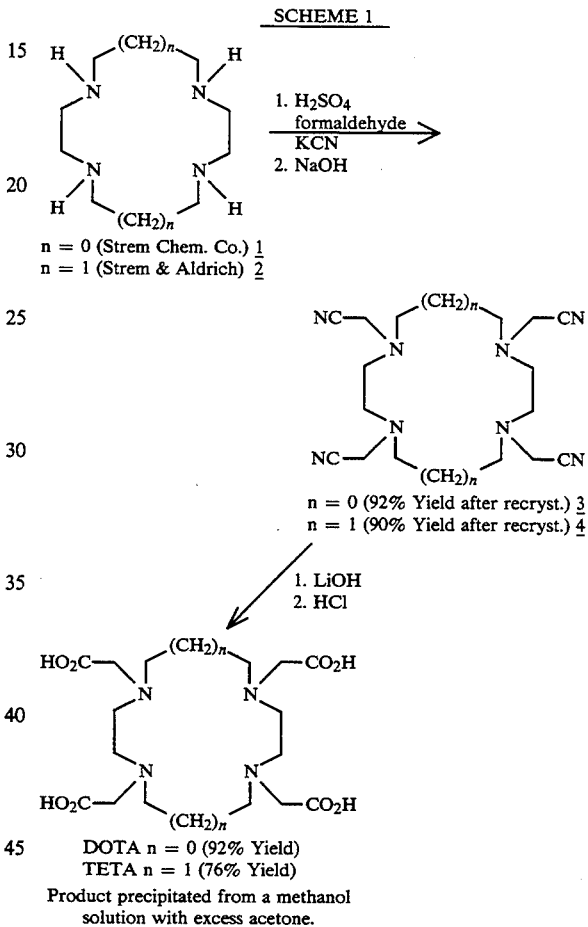

SCHEME 1 n = 0 (Strem Chem. Co.) 1
n = 1 (Strem & Aldrich) 2 n = 0 (92% Yield after recryst.) 3
n = 1 (90% Yield after recryst.) 4

DOTA n = 0 (92% Yield)
TETA n = 1 (76% Yield)
Product precipitated from a methanol solution with excess acetone.

Commercial macrocycles 1, and 2 are cyanomethylated using acid such as sulfuric acid, formaldehyde and cyanide compound such as potassium cyanide or sodium cyanide to give cyanonitriles 3 and 4. 3 and 4 are hydrolyzed using base such as lithium hydroxide followed by acidification with acid such as HCl, evaporation to dryness, reconstitution in alcohol, e.g., methanol and precipitation, e.g., with acetone give DOTA and TETA respectively. The DOTA and TETA may be used to chelate metals, particularly radiometals.

Temperature, time and molar ratios of reactants in the two steps depicted in Scheme I are not critical and may be easily determined by the skilled artisan. For purposes of economy and efficiency, the reaction of the first step is carried out under temperature conditions which take into account the heat of hydration. The time of the first step may be judged by the presence of precipitate and may be, for example, from about 24 to about 48 hours. The formaldehyde and cyanide compound are provided in excess of the amount of cyclams 1 and 2, preferable in a molar ratio of at least four moles each of formaldehyde and cyanide compound per mole of cyclam. The molar ratio of acid in the first step is preferably about two moles per mole of cyclam.

Likewise in the second step hydrolysis, temperature, time and molar ratios of reactants are not critical. A temperature for reflux conditions is utilized, e.g. about 80° C. to about 90° C. The reaction may be followed by NMR to completion, for example, to about two days. The base is provided in a molar ratio of at least four moles base per mole of cyclam. Sufficient acid is used to bring the pH to an acid range, preferably to about pH 1–3.

The chelating agents may be derivatized by converting an average of one carboxylic acid on the chelate to an activated ester which is capable of reacting with either an amine or a sulfhydryl group on a biological binding agent. The derivatization is Shown in Scheme 2:

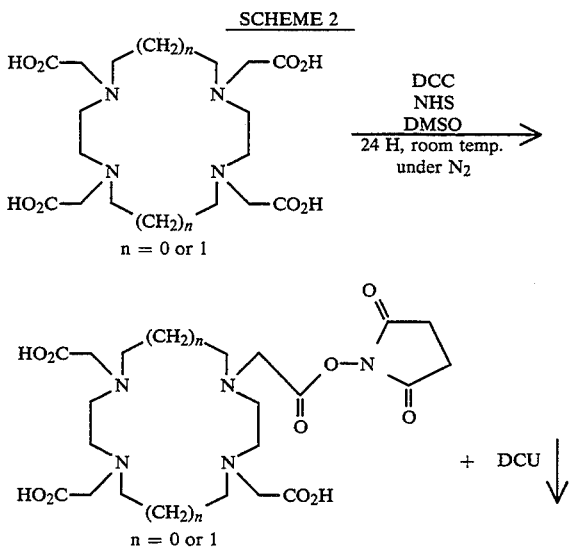

DCC=dicyclohexylcarbodiimide
NHS=N-hydroxysuccinimide
DMSO=dimethylsulfoxide
DCU=dicyclohexyl urea Derivatization of a carboxylic acid resulting in ester formation at the carboxylic acid site may be achieved using, for example, one molar equivalent of DOTA or TETA and 0.5 equivalent dicyclohexylcarbodiimide and N-hydroxysuccinimide in a solvent such as dimethyl sulfoxide (DMSO). This solution may be stored for extended periods of time, e.g. up to two months at or more 0° C., without loss of reactivity.

The ligands, i.e., the chelating agents, may be conjugated to biological binding agents. Biological binding agents to which the chelating agents may be conjugated include substances capable of localizing in vitro or in vivo to a tumor or neoplasia. Neoplasia may occur, for example, in animals such as mammals including humans. Neoplasia is progressive, uncontrolled cell division which, if progeny cells remain localized, at least initially, results in the formation of an abnormal growth called a tumor or neoplasm. A neoplasm may be malignant or benign. A malignant neoplasm invades adjacent tissues and may metastasize. A neoplastic growth is generally considered to be a non-inflammatory mass formed by the growth of new cells and having no physiologic function. The conjugated radiometal chelates of the invention can be formulated per se in pharmaceutical preparation or formulated in the form of pharmaceutically acceptable salts. These preparations can be prepared according to conventional chemical methods. Anti-tumor agents such as cis-platin or bleomycin have been used therapeutically in humans to interfere with rapid cell division which occurs in neoplasia. Radionuclides have also been used for the detection and/or selective destruction of tumors localized through the use of monoclonal antibodies.

Therefore, the derivatized macrocyclic polyaminocarboxylate metal chelating agents may be conjugated with various biological binding agents for localizing to the desired area. The biological binding agents may include antibodies (polycolonal and monoclonal), antibody fragments, e g the F(ab')$_2$, Fab', or Fc portions of an immunoglobulin Ig, other proteins, protein fragments or peptides, genetically engineered proteins, peptides and antibodies, single chain antibodies, small molecular recognition units, polysaccharides, nucleic acids, steroids, enzymes, drugs, vitamins, and a number of other biologically active compounds.

The method of the invention was found to be superior to common methods previously used in the art for labeling antibody using other functionalized polyaminocarboxylates such as diethylenetriamine pentaacetic acid (DTPA) anhydride (Hnatowich et al., Science 220:613, 1983). Radiometals can be complexed with the chelating agent-biological binding agent conjugates.

Based on various criteria such as imaging photons, particle emission, dosimetry, and feasibility of production, a number of radiometals are considered suitable for labeling antibodies for radioimmunoimaging (RII) and/or radioimmunotherapy (RIT) (Mausner and Srivastava, Med. Phys. 1993, in press). Examples of suitable radiometals are: $^{55}$Co, $^{64}$Cu, $^{66}$Ga, $^{68}$Ga, $^{97}$Ru, $^{99m}$Tc, $^{111}$In, and $^{203}$Pb for imaging, and $^{47}$Sc, $^{67}$Cu, $^{90}$Y, $^{105}$Rh, $^{109}$Pd, $^{153}$Sm, $^{177}$Lu, $^{188}$Re, $^{199}$Au, and $^{212}$Bi for radiotherapy. While the chelating agents of this invention will produce more stable complexes with most above radiometals, $^{55}$Co, $^{64}$Cu, $^{67}$Cu, $^{111}$In, $^{203}$Pb, $^{90}$Y, and $^{153}$Sm would benefit most because of their coordination geometries,, and because they require bifunctional chelating agents which bind the radiometal with a higher denticity (number of coordination sites) and/or incorporate greater structural rigidity, in order to produce immunoconjugates with better in-vivo kinetic stability.

Although some radiometals have been shown to produce good biodistribution using modified polyaminocarboxylates, e.g. DTPA functionalized at the carbon backbone (Harrison, et. al., Nucl. Med. Biol. 18:469, 1991; Gansow, Nucl. Med. Biol. 18:369, 1991) nonspecific uptake of radioactivity has been undesirably high in bone and kidney with $^{203}$Pb and in bone and liver with $^{90}$Y.

Biodistribution studies showed that Y, Pb and Cu-DOTA chelates conjugated with antibody had better biodistribution than CTTHA (N,N'-(2-aminoethyl)-trans-1,2-diaminocyclohexane-N,N',N'',N''',N'''',N''''-hexaacetic acid), CDTPA (cyclohexyl diethylenetriamine-pentaacetic acid or N-(2-aminoethyl)-trans 1,2-diamino cyclohexane-N,N', N',N'',N'', pentaacetic acid), 4-ICE (4-isothiocyanato-trans-1,2-diaminocyclohexane-N,N,N',N'-tetraacetic acid), CDTAMA (trans-1,2-diaminocyclohexane-N,N,N',N'-tetraacetic acid monoanhydride), and DTPADA (the bicyclic anhydride of DTPA) (control). The cyclohexyl ligands CTTHA, CDTPA, 4-ICE, and CDTAMA are described in U.S. Pat. Nos. 5,021,571 and 5,089,663. Synthesis of 4-ICE is described in U.S. patent application Ser. No. 867,533 filed Apr. 13, 1992.

As non-limiting examples, two antibody systems were investigated: anticolon carcinoma MAb 17-1A (whole IgG and F(ab')$_2$ fragment) and an anti-CEA F(ab')$_2$ preparation. The average number of ligands per MAb varied between 1 and 3. In a typical case, contacting a 60/1 molar ratio of activated ligand/17-1A IgG in 0.1M NaHCO$_3$ at room temperature for two hours yielded 2-3 ligands/MAb with negligible cross-linking (1% by HPLC). $^{88}$Y, $^{67}$Cu and $^{203}$Pb labeled DOTA-17-1A and $^{67}$Cu-TETA-17-1A were stable in serum (1-4% loss after 4 days).

Biodistribution studies were performed in human tumor xenografted nude mice. As an example, $^{88}$Y-17-1A immunoconjugates showed progressive improvement as follows: DOTA≧CTTHA≧CDTPA>-4ICE>>CDTAMA>>DTPADA. Based on these and similar data, it can be concluded that both denticity and the rigidity of the bifunctional chelating agent are important factors that contribute to higher in-vivo stability of many radiometal immunoconjugates, especially those of Cu, Pb, Y, and other rare earths. Monofunctionalized DOTA, a rigid ligand with 7 coordination sites, appears to provide the best combination of the ligands studied above.

The chelates of the invention may also be used in Emission Tomography to measure physiological function of organs and related biochemical processes in both health and disease. The two modes of emission tomography are single-photon emission computed tomography (SPECT) and positron emission tomography (PET). SPECT uses radionuclides that emit a single photon of a given energy and these include gamma ray emitters such as $^{67}$Ga, $^{97}$Ru, $^{99m}$Tc, $^{111}$In, $^{123}$I, $^{131}$I, $^{203}$Pb, and others. PET uses radionuclides known as positron emitters such as $^{11}$C, $^{15}$O, $^{18}$F, $^{55}$Co, $^{64}$Cu, $^{68}$Ga, $^{75}$Br, $^{89}$Zr, $^{124}$I, and others for coincidence detection in which the positron and electron annihilate each other to form two photons at 180° angle from each other. In SPECT and PET, transverse section reconstruction of the radionuclide distribution within the body is obtained by acquiring images of multiple slices of the organ or the whole body. The chelates of the invention can be used for SPECT and PET imaging studies of the physiology, function, and biochemistry of tumors, and other organs and tissues.

The invention is illustrated by the following non-limiting examples.

EXAMPLE 1

Synthesis of N,N',N'',N'''-Tetracyanomethylene-1,4,7,10-tetraazacyclododecane

A solution of 3.0 g (9.4 mmol) 1,4,7,10-tetraazacyclododecane tetrahydrochloride in 10 ml H$_2$O was stirred and cooled to 0°-2° C. To this was slowly added 1.05 ml (18.8 mmol) concentrated H$_2$SO$_4$ followed by 3.52 ml of 37% formaldehyde. Over a period of one hour a solution consisting of 2.7g (41 mmol) potassium cyanide dissolved in 15° ml H$_2$O was added. The reaction was then allowed to warm to room temperature and stirred for 24 H. During this time a white precipitate formed. The reaction was then made basic (pH≈10) by the addition of 3M NaOH. As the mixture was neutralized the precipitate dissolved and re- precipitated when the pH was greater than 8. The solid was collected, washed with H$_2$O, dried under vacuum and recrystallized from a mixture of ethylacetate/acetone to give two crops of a white solid totaling 2.9 g (92%) mp 157°-159° C.

IR (mineral oil) 2210 cm$^{-1}$ NMR (60 MHz)(CD$_3$)$_2$SO and CDCl$_3$ with 1% TMS δ2.60 (s,16H) δ3.67 (s,8H) Elemental Analysis Calc: C, 58.52; H, 7.37; N, 34.12; Found: C, 58.56; H, 7.38; N, 34.05;

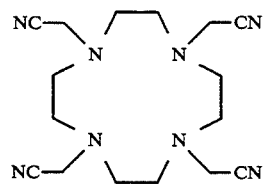

EXAMPLE 2

Synthesis of 1,4,7,10-Tetraazacyclododecane-N,N',N'',N'''-tetraacetic acid

To a solution of 2.5 g (7.7 mmol) N,N',N'',N'''-tetracyanomethylene-1,4,7,10-tetraazacyclododecane as prepared in Example 1 and dissolved in 30 ml methanol was added 150 water and 3.9 g (93 mmol) lithium hydroxide monohydrate. This solution was allowed to gently reflux in an open 500 ml round bottom flask for two days. Water was added as needed to maintain the solution level at 100 ml. The reaction was cooled to room temperature, acidified to pH 2 by the addition of 3M HCl, and concentrated to a sticky residue. The residue was dried by the addition of methanol followed by concentration to dryness. This was repeated twice more. The dry powdery residue was dissolved in 30 ml MeOH and added dropwise to a stirred solution of 300 ml acetone. The precipitated product was collected, washed with acetone, and dried under vacuum to give 3.4 g (92%) of a white solid.

IR (mineral Oil) 1.710 cm$^{-1}$, 1630 cm$^{-1}$ NMR (60 MHz)D$_2$O+NaOD, pH~14) δ3.07 (s,8), 2.63 (s,16)

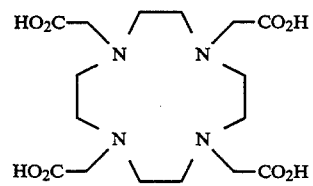

EXAMPLE 3

Synthesis of N,N',N'',N'''-Tetracyanomethylene-1,4,8,11-tetraazacyclotetradecane To a solution of 8.33 ml concentrated HCl in 20 ml H$_2$O was added 5.0 g (25 mmol) cyclam. This solution was stirred and cooled to 0°-2° C. in an ice bath. To this solution was added slowly 2.8 ml concentrated H$_2$SO$_4$ followed by 9.4 ml 37% formaldehyde. Next, a solution consisting of 7.2 g (110 mmol) potassium cyanide dissolved in 20 ml H$_2$O was added over a period of one hour. The reaction was allowed to warm to room temperature and stirred for 24 H. During this time a white precipitate formed. The reaction mixture was then made basic (pH 10) by the addition of 3M NaOH. As the mixture was neutralized the solid in the reaction dissolved and reprecipitated when the pH was greater than 8. The solid was collected, washed with H$_2$O, dried under vacuum to give 8.3 g (94%) of a white solid. The filtrate was extracted with CH$_2$Cl$_2$ and the CH$_2$Cl$_2$ extracts combined, dried with MgSO$_4$ and concentrated to give 0.4 g (4%) of an off white solid. The solids were combined and recrystallized from ethylacetate/acetone to give 3 crops of crystals totaling 8.18 g (92%). mp 170°–172° C.

IR mineral oil 2210 cm$^{-1}$ NMR (60 MHz)(CD$_3$)$_2$SO+CDCl$_3$+1% TMS δ3.67 (s,8), 2.5 (s,16), 1.8–1.3 (m,4) Elemental Analysis Calc: C, 60.65; H, 7.92; N, 31.43; Found: C, 60.65; H, 7.98; N, 31.36;

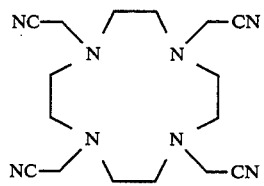

EXAMPLE 4

Synthesis of 1,4,8,11-Tetraazacyclotetradecane-N,N',N'',N'''-tetraacetic acid

To a solution of 7 0 g N,N',N'',N'''-tetracyanomethylene-1,4,8,11-tetraazacyclotetradecane (19.7 mmol) as prepared in Example 3 and dissolved in 40 ml methanol was added 200 ml H$_2$O and 9.9 g lithium hydroxide monohydrate (236 mmol). This solution was allowed to reflux gently in an open 500 ml round bottom flask for two days. Water was added as needed to keep the solution level at approximately 150 ml. The reaction was cooled to room temperature, acidified to pH 2 by the addition of 3M HCl and evaporated to a sticky solid. The solid was dried by being dissolved in methanol and again evaporated to dryness. Additional methanol was added and the solution evaporated to dryness. This was repeated a third time. The residue was dissolved in 40 ml methanol and added dropwise to a stirred solution of acetone (400 ml). The precipitated product was collected, washed with acetone, and dried under vacuum to give 7.9 g (91%).

IR (mineral oil) 1635 cm$^{-1}$ NMR (60 MHz )( D$_2$O+NaOD) δ1.97–1.33 (m,4), 2.63 (s,16), 3.07 (s,8)

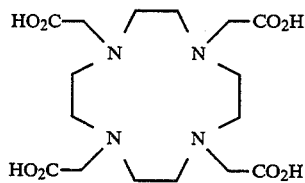

Examples 1–4 show that the method of the invention is simple, efficient, and results in high product yield of over 90%.

EXAMPLE 5

The serum stability of radiometal conjugates of DOTA and TETA was determined and the data are summarized in Table 1. Additional data using other ligands DTPADA and 4-ICE are included for comparison.

TABLE 1

Serum Stability of Radiometal Conjugates

| Radiometal | Conjugate | Radioactivity with Conjugate (HPLC) | |
|---|---|---|---|
| | | 1D | 4D |
| Lead-203 | Anti-CEA-F(ab')$_2$-DOTA | 100 | 100 |
| | Anti-CEA-F(ab')$_2$-4-ICE | 71 | 5 |
| Yttrium-88 | 17-1A-IgG-DOTA | 98 | 96 |
| | 17-1A-IgG-DTPADA | 57 | 15 |
| | 17-1A-IgG-4-ICE | 48 | 14 |
| Copper-67 | 17-1A-IgG-DOTA | 99 | 96–99 |
| | 17-1A-IgG-TETA | 97 | 98 |
| | 17-1A-IgG-DTPADA | 57 | 15 |
| | 17-1A-IgG-4-ICE | 48 | 14 |

EXAMPLES 6–27

Immunoconjugates of Lead-203 and Yyttrium-88

The following polyaminocarboxylates (PACS) were evaluated and compared: (1) cyclohexyl EDTA monoanhydride (CDTAMA); (ii) 4-isothiocyanato-cyclohexyl EDTA (4-ICE); (iii) cyclohexyl DTPA (CDTPA); (iv) cyclohexyl TTHA (CTTHA); and (v) 1,4,7,10-tetraazacyclododecane N,N', N'',N'''-tetraacetic acid (DOTA). Cyclohexyl PACS were synthesized and functionalized using procedures described in U.S. Pat. Nos. 5,021,571 and 5,089,663. Conjugation to MAb was done .either through a monofunctionalized derivative (CDTAMA, CDTPA-NHS, CTTHA-NHS) or through the 4-SCN group (4-ICE). DOTA was synthesized using the new procedure utilizing cyanomethylation of commercial 1,4,7,10-tetraazacyclododecane followed by hydrolysis. (Scheme 1) and conjugated to MAb through one of the carboxylates that was converted to an NHS ester (R. G. Buckley and F. Searle, FEBS 166:202, 1984). DTPADA was used as a control ligand in all experiments.

Two antibody systems were investigated: anticolon carcinoma MAb 17-1A (Y and Pb) and an anti-CEA F(ab')$_2$ preparation (Pb only). The average number of ligands per MAb varied between 1 and 3. Lead-203 was obtained from Nordion International as a solution in HCl (sp. act. 1.0 mCi/μg), and no-carrier-added $^{88}$Y (used as a stand-in for $^{90}$Y for convenience) from Los Alamos National Laboratory. Centricon-purified immunoconjugates were labeled with Pb and Y at pH 5–6 (acetate or citrate buffers) and then purified further by size-exclusion HPLC. Labeling yields for the various preparations ranged between 40 and 80% (except −10% for Pb-DOTA, Y-CDTPA, and Y-CTTHA). Serum stability was determined from in-vitro incubations for up to 5 d. Biodistribution studies were performed in human tumor xenografted nude mice. The results are shown in Table 2 below and in FIGS. 1a, 1b, 2a and 2b.

Table 2 shows tissue distribution of $^{203}$Pb immunoconjugates in mice at 24 hours and 96 hours (Examples 6–15).

Figure 1B:
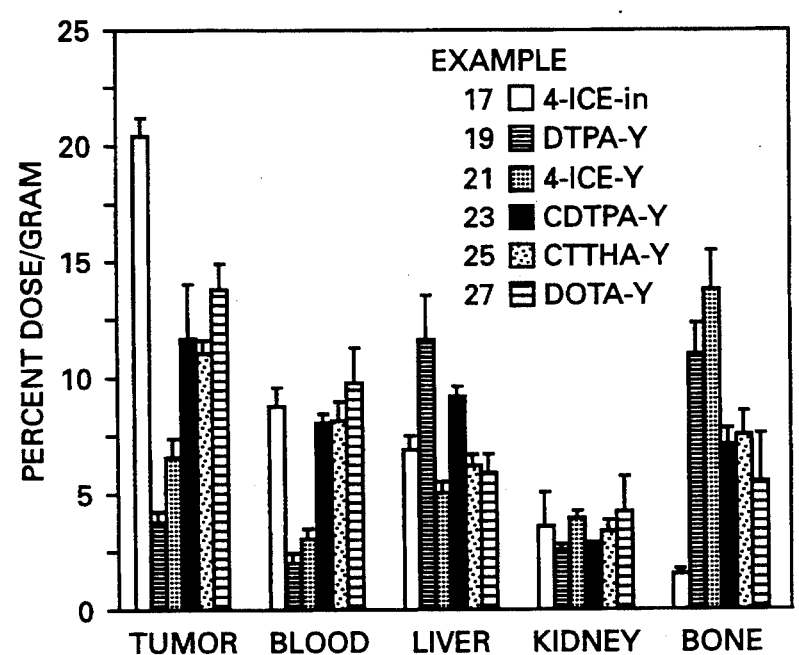

FIGS. 1a and 1b show tissue distribution of $^{88}$Y-17-1A immunoconjugates in SW-948 human colon carcinoma xenografted nude mice at 24 hours (left) and 96 hours (right) (Examples 18–27). $^{111}$In-4-ICE-17-1A data are included for comparison (Examples 16 and 17).

Figure 2A:
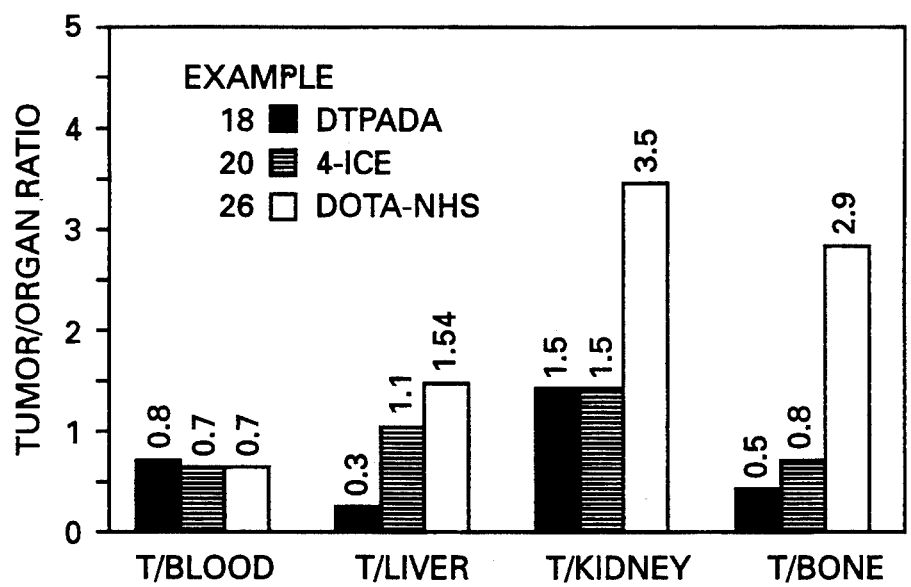
FIGS. 2a and 2b are bar graphs showing additional comparative data.
Figure 2B:
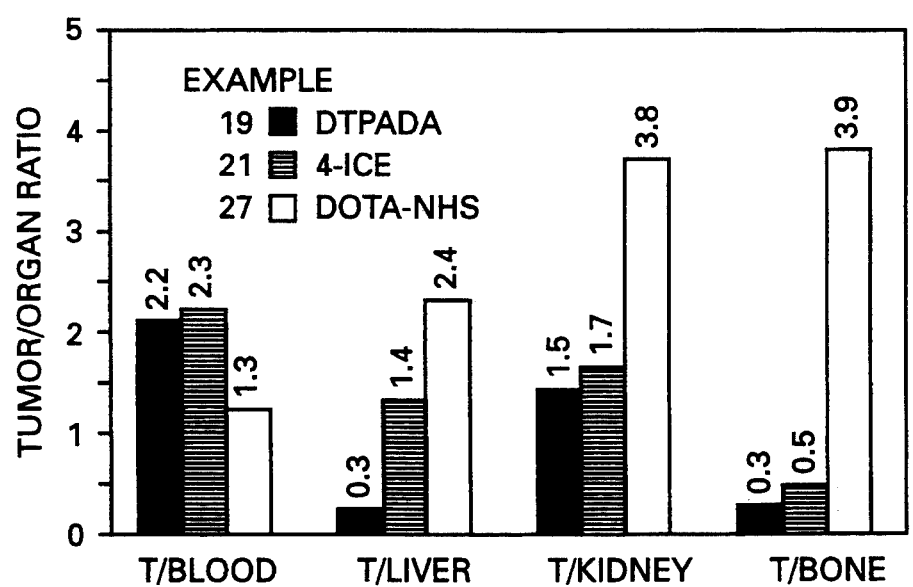

FIGS. 2a and 2b show tumor to organ ratios of $^{88}$Y-17-1A IgG in Mice at 24 hours (left) and 96 hours (right) (Examples 18, 19,, 20, 21, 26 and 27).

Ligand abbreviations in these data are explained in the text.

TABLE 2

Tissue Distribution of $^{203}$Pb Immunoconjugates in Nude Tumor mice*

| Ex. | Conjugate** | Time, Hr | Tumor | Blood | Liver | Kidney | Bone | Whole (% Dose) |
|---|---|---|---|---|---|---|---|---|
| 6 | $^{203}$Pb Nitrate (control) | 24 | 0.4 ± 0.2 — | 7.7 ± 1.5 (0.05) | 6.0 ± 0.5 (0.07) | 27.6 ± 1.0 (0.01) | 12.1 ± 0.7 (0.03) | 58 |
| 7 | | 48 | 0.4 ± 0.2 — | 1.8 ± 0.3 (0.22) | 3.3 ± 0.7 (0.12) | 15.2 ± 1.7 (0.03) | 13.3 ± 1.1 (0.03) | 61 |
| 8 | DTPA-DA-17-1A (10%, 1d) | 24 | 1.1 ± 0.2 — | 3.6 ± 0.1 (0.3) | 5.3 ± 0.2 (0.2) | 18.6 ± 4.3 (0.06) | 13.0 ± 1.6 (0.08) | 61 |
| 9 | | 96 | 0.4 ± 0.1 — | 0.9 ± 0.1 (0.4) | 2.7 ± 0.4 (0.15) | 6.3 ± 1.5 (0.06) | 8.1 ± 0.3 (0.05) | 35 |
| 10 | CDTA-MA-17-1A (50%, 1d) | 24 | 6.1 ± 0.2 — | 8.6 ± 0.9 (0.7) | 6.4 ± 0.7 (1.0) | 16.5 ± 0.7 (0.4) | 12.1 ± 0.4 (0.5) | 77 |
| 11 | | 96 | 1.1 ± 1.1 — | 1.3 ± 0.3 (0.9) | 2.2 ± 0.3 (0.5) | 6.5 ± 0.2 (0.2) | 14.1 ± 1.5 (0.08) | 48 |
| 12 | 4-ICE-CEA F(ab')$_2$ (71%, 1d) | 24 | 7.7 ± 1.2 — | 4.7 ± 0.7 (1.6) | 8.5 ± 0.9 (0.9) | 19.1 ± 2.2 (0.4) | 7.6 ± 0.7 (1.0) | 76 |
| 13 | | 96 | 2.3 ± 0.5 — | 1.6 ± 0.2 (1.5) | 3.0 ± 0.4 (0.8) | 8.1 ± 0.8 (0.3) | 11.0 ± 1.3 (0.2) | 46 |
| 14 | DOTA-CEA F(ab')$_2$ (100%, 5d) | 24 | 19.3 ± 4.6 — | 3.1 ± 0.6 (6.3) | 9.8 ± 1.5 (2.0) | 30.0 ± 5.0 (0.6) | 1.6 ± 0.2 (12) | 94 |
| 15 | | 96 | 12.2 ± 2.1 — | 0.14 ± 0.01 (87) | 3.7 ± 0.4 (3.3) | 14.9 ± 1.0 (0.8) | 1.0 ± 0.1 (12) | 48 |

*Data (% dose per g) are average of 3–10 animals ± 1 std. deviation. Tumor to tissue ratios are included in parentheses. All preparations were HPLC purified and monomeric fractions were injected i.v. into the mice. SW 948 colon carcinoma xenografts were used for 17-1A experiments and LS-174T xenografts for the anti-CEA experiments.
**Ligand abbreviations are explained in the text. In-vitro serum stability at 37° C. shown in parentheses under the conjugate.

The results show that in the case of $^{203}$Pb immunoconjugates with 17-1A IgG (Table 1), CDTAMA produced higher blood and whole body levels and increased tumor uptake compared to DTPADA. Bone and kidney uptake, however, remained high. In the CEA-F(ab')2 system, the rigid DOTA gave higher tumor to non-tumor ratios (Table 1) compared with the semi-rigid 4-ICE (T/blood, T/liver, T/bone, T/kidney at 96 hr: 87 vs 1.5; 3.3 vs 0.8; 12.0 vs 1.3; 0.8 vs 0.3, respectively). Biodistribution studies with $^{88}$Y-17-1A immunoconjugates (FIGS. 1 and 2) showed progressive improvement as follows: DOTA≧CTTHA≧CDTPA>4ICE>>CDTAMA>>DTPADA.

These results also demonstrate that common methods for labeling MAb using functionalized polyaminocarboxylates, such as the DTPA dianhydride (DTPADA) and others, are not ideal for use with $^{203}$Pb and $^{90}$Y. These radiometals share a common feature in that they require bifunctional chelating agents with a higher denticity (number of coordination sites) and greater structural rigidity in order to obtain immunoconjugates with better in-vivo kinetic stability. Although some radiometals produce improved biodistribution using DTPA functionalized at the carbon backbone (A. Harrison et al., Nucl. Med. Biol. 18:469 (1991); O. A. Gansow, Nucl. Med. Biol. 18:369 (1991)), non-specific uptake of radioactivity is still undesirably high in bone and kidney with $^{203}$Pb and in bone and liver with $^{90}$Y.

Based on these data, it is concluded that both denticity and the rigidity of the bifunctional chelating agent are important factors that contribute to higher in-vivo stability of Y and Pb radioimmunoconjugates (Tables 3–5). Monofunctionalized DOTA, a rigid ligand with 7 coordination sites appears to provide the best combination and warrants further investigation for use with $^{203}$Pb and $^{90}$Y.

TABLE 3

Effect of denticity (coordination sites) and structural rigidity of the ligand on the 96 hr biodistribution of $^{203}$Pb and $^{88}$Y immunoconjugates in nude tumor mice*

| Immunoconjugate | Denticity | Rigidity | $^{203}$Pb T** | $^{203}$Pb T/L | $^{203}$Pb T/B | $^{88}$Y T** | $^{88}$Y T/L | $^{88}$Y T/B |
|---|---|---|---|---|---|---|---|---|
| DTPADA-17-1A | 7 | No | 0.40 | 0.15 | 0.05 | 3.6 | 0.32 | 0.34 |
| CDTAMA-17-1A | 5 | Semi-rigid | 1.1 | 0.50 | 0.08 | — | — | — |
| 4-ICE-17-1A | 6 | Semi-rigid | — | — | — | 6.4 | 1.4 | 0.48 |
| 4-ICE-CEA-F(ab')$_2$ | 6 | Semi-rigid | 2.3 | 0.80 | 0.20 | — | — | — |
| CDTPA-NHS-17-1A | 7 | Semi-rigid | — | — | — | 11.4 | 1.3 | 1.7 |
| CTTRA-NHS-17-1A | 9 | Semi-rigid | — | — | — | 10.8 | 1.9 | 1.5 |
| DOTA-NHS-17-1A | 7 | Rigid | — | — | — | 13.5 | 2.4 | 2.6 |
| DOTA-CEA-F(ab')$_2$ | 7 | Rigid | 12.2 | 3.3 | 12 | — | — | — |

*Data shown are average of 3–10 mice per experiment. T-tumor; B-bone; L-liver. Ligand abbreviations are explained in the text. Other experimental details same as in Table 1.
**Tumor uptake in % injected dose per g.

TABLE 4

Improvement in Tumor/Organ Ratios of $^{203}$Pb Immunoconjugates DOTA-NHS vs. 4-ICE*

| Ratio, tumor to: | Time (Hr) | 4-ICE | DOTA-NHS | Improvement Factor DOTA-NHS/4-ICE |
|---|---|---|---|---|
| Blood | 24 | 1.6 | 6.3 | 3.9 |
|  | 96 | 1.5 | 87 | 58 |
| Liver | 24 | 0.9 | 2.0 | 2.2 |
|  | 96 | 0.8 | 3.3 | 4.1 |
| Kidney | 24 | 0.4 | 0.6 | 1.5 |
|  | 96 | 0.3 | 0.8 | 2.7 |
| Bone | 24 | 1.0 | 12 | 12 |
|  | 96 | 0.2 | 12 | 60 |
| % dose per | 24 | 7.7 | 19.3 | 2.5 |

TABLE 4-continued

Improvement in Tumor/Organ Ratios of $^{203}$Pb Immunoconjugates DOTA-NHS vs. 4-ICE*

| Ratio, tumor to: | Time (Hr) | 4-ICE | DOTA-NHS | Improvement Factor DOTA-NHS/4-ICE |
|---|---|---|---|---|
| g in tumor | 96 | 2.3 | 12.2 | 5.3 |

*Data using Anti-CEA-F(ab')$_2$ antibody; LS-174T tumor xenografts in nude mice.

TABLE 5

Improvement in Tumor/Organ Ratios $^{88}$Y Immunoconjugates DOTA-NHS vs. DTPA*

| Ratio, tumor to: | Time (Hr) | 4-ICE | DOTA-NHS | Improvement Factor DOTA-NHS/4-ICE |
|---|---|---|---|---|
| Blood | 24 | 0.8 | 0.8 | 1.0 |
|  | 96 | 2.2 | 1.9 | 0.9 |
| Liver | 24 | 0.3 | 1.7 | 5.7 |
|  | 96 | 0.3 | 3.3 | 11 |
| Kidney | 24 | 1.5 | 3.7 | 2.5 |
|  | 96 | 1.5 | 6.2 | 4.1 |
| Bone | 24 | 0.5 | 2.8 | 5.6 |
|  | 96 | 0.3 | 3.5 | 11.7 |
| dose per | 24 | 5.2 | 11.0 | 2.1 |
| g in tumor | 96 | 3.5 | 10.0 | 2.9 |

*Data using anticolon ca Mab 17-1A; SW-948 tumor xenografts in nude mice

EXAMPLES 28-56

Immunoconjugates of Copper-64, Copper-67, and Samarium-153

Whole IgG or F(ab')$_2$ fragments of anticolon carcinoma antibody 17-1A were conjugated with the macrocyclic ligands 1,4,7,10-tetraazacyclododecane N,N',N'',N'''tetraacetic acid (DOTA, synthesis described in scheme 1); 1,4,8,11-tetraazacyclotetradecane N,N',N'',N'''tetraacetic acid (TETA, synthesis described in scheme 2), and with DTPA, 4-ICE, CDTPA, and CTTHA using either a monofunctionalized derivative (CDTPA-NHS, CTTHA-NHS), through the 4-SCN group (4-ICE), or the dianhydride (DTPA). DOTA and TETA were conjugated to MAb through one of the carboxylates that was converted to an NHS ester (Buckley et al., FEBS 166:202, 1984). Radiolabeling with copper was carried out by incubating the $^{67}$Cu or $^{64}$Cu chloride solution in 0.05N HCl with the conjugates in 0.1M sodium bicarbonate, pH 8.4 buffer, with 0.1M acetate as the weakly chelating buffer system. Purification was carried out by HPLC using a Zorbax-GF250 sizing column and 0.1M, pH 7.0 phosphate buffer as the eluent. EDTA (10 μl of a 0.05M solution) was used to remove unbound and/or non-specifically bound radioactivity. Labeling efficiencies were 80–90% for all conjugates and immunoreactivity retention ranged between 60–90%, as determined from live cell-binding assays using SW-948 human colon carcinoma cells.

Serum stability studies were performed to determine the relative efficiency of the various ligands for chelating copper. The labeled conjugates were incubated in mouse serum at 37° C. for up to 5 d. Aliquots were removed and injected onto a Zorbax GF-250 HPLC column and eluted with 0.1M phosphate buffer, pH 7.0, at a flow rate of 1 ml/min. Fractions (6 drops each) were collected and counted for radioactivity using a gamma counter. The percent of injected activity that eluted with the antibody was determined. DOTA and TETA conjugates showed 90-95% stability after 96 h whereas 4-ICE conjugate retained only 39% MAb-bound activity, after 24 hours. All conjugates retained 95-99% of the copper as MAb-bound activity when incubated in saline only, for up to 96 hours.

Biodistribution of $^{67}$Cu and $^{64}$Cu labelled conjugates of 17-1A (IgG and F(ab')$_2$) was determined in normal (Balb/c) mice as well as human colon carcinoma (SW 948 cells) xenografted nude mice. Representative data are summarized in Tables 6 and 7. Four to five animals were used per time point for each radiolabelled preparation. The animals were sacrificed at 24 and 96 h (or other time periods) following the i.v. administration of the various immunoconjugates.. In-vivo stability in normal mice was in the order DOTA≈TETA>>4-ICE (Table 6). As expected, F(ab')$_2$ conjugates cleared faster from blood than IgG conjugates. Results in tumor-bearing nude mice are summarized in Table 6 along with tumor to normal tissue ratios. DOTA conjugates gave higher tumor uptakes than the TETA conjugates. The $^{67}$Cu-IgG-DOTA conjugate yielded the highest tumor uptake at 96 h and thus the tumor to organ ratios were higher than with other conjugates. F(ab')$_2$ conjugates again, as expected, cleared faster than the whole IgG conjugates. Results with $^{64}$Cu for all the conjugates were generally similar to those with $^{67}$Cu.

TABLE 6

Biodistribution of $^{67}$Cu Labeled Anticolon Carcinoma Monoclonal Antibody 17-1A in Normal Mice$^a$.

| Ex. | Conjugate$^b$ | Time (h) | Blood | Kidney | Liver | Whole Body Retention$^c$ |
|---|---|---|---|---|---|---|
| 28 | 4-ICE-IgG | 24 | 2.7 ± 0.4 | 9.2 ± 0.7 | 18 ± 0.4 | 80 ± 3 |
| 29 |  | 96 | 1.2 ± 0.1 | 7.1 ± 0.6 | 10.3 ± 0.8 | 50 ± 3 |
| 30 | DOTA-1NHS-IgG | 24 | 18.5 ± 1.9 | 4.8 ± 0.3 | 8.7 ± 0.4 | 83 ± 6 |
| 31 |  | 96 | 12.9 ± 0.5 | 4.2 ± 0.2 | 7.0 ± 0.9 | 68 ± 3 |
| 32 | TETA-1NHS-IgG | 24 | 15.4 ± 0.3 | 5.4 ± 0.2 | 7.7 ± 0.4 | 88 ± 4 |
| 33 |  | 72 | 11.1 ± 1.1 | 5.0 ± 0.4 | 6.3 ± 0.5 | 73 ± 4 |
| 34 | 4-ICE-F(ab')$_2$ | 24 | 1.7 ± 0.1 | 6.2 ± 0.3 | 11.8 ± 0.6 | 56 ± 3 |
| 35 |  | 96 | 0.8 ± 0.1 | 4.3 ± 0.4 | 6.1 ± 0.5 | 32 ± 3 |
| 36 | DOTA-1NHS-F(ab')$_2$ | 24 | 8.0 ± 0.5 | 7.0 ± 1.0 | 8.3 ± 0.8 | 83 ± 5 |
| 37 |  | 96 | 1.0 ± 0.1 | 4.1 ± 0.2 | 6.4 ± 0.4 | 42 ± 2 |
| 38 | TETA-1NHS-F(ab')$_2$ | 24 | 2.0 ± 0.1 | 55.5 ± 2.9 | 8.0 ± 0.3 | 75 ± 1 |
| 39 |  | 96 | 0.5 ± 0.1 | 18.3 ± 1.5 | 4.6 ± 0.1 | 35 ± 1 |

$^a$% Injected dose/g; n = 5
$^b$Whole IgG used except as indicated
$^c$% Injected dose remaining

TABLE 7

Biodistribution[a] of $^{67}$Cu Labeled Anticolon Carcinoma Monoclonal Antibody 17-1A in Human Tumor (SW 948 cells) Xenografted Nude Mice.

| Ex. | Conjugate | Time (h) | Tumor | Blood | Kidney | Liver | Whole Body Retention[b] |
|---|---|---|---|---|---|---|---|
| 40 | DOTA-1NHS-IgG | 24 | 11.2 ± 1.3 | 15.5 ± 1.2 (0.7) | 1.4 ± 0.3 (2.4) | 9.4 ± 0.9 (1.2) | 112 ± 7 |
| 41 |  | 96 | 13.5 ± 1.5 | 10.6 ± 1.6 (1.3) | 4.9 ± 0.2 (3.0) | 7.0 ± 0.8 (2.1) | 84 ± 6 |
| 42 | DOTA-1-NHS-F(ab')$_2$ | 24 | 10.3 ± 2.2 | 9.4 ± 0.6 (1.1) | 14.7 ± 0.7 (0.7) | 15.4 ± 0.7 (0.7) | 122 ± 2 |
| 43 |  | 96 | 5.2 ± 0.4 | 1.3 ± 0.2 (4.0) | 7.5 ± 0.6 (0.7) | 7.5 ± 0.6 (0.7) | 57 ± 3 |
| 44 | TETA-1-NHS-IgG | 24 | 10.3 ± 0.7 | 16.8 ± 1.0 (0.6) | 4.9 ± 0.3 (2.1) | 8.6 ± 0.7 (1.2) | 103 ± 4 |
| 45 |  | 96 | 7.5 ± 1.2 | 9.4 ± 0.7 (0.8) | 4.6 ± 0.2 (1.6) | 6.4 ± 0.3 (1.2) | 74 ± 5 |
| 46 | TETA-1-NHS-F(ab')$_2$ | 24 | 9.3 ± 2.4 | 12.8 ± 0.6 (0.7) | 8.8 ± 0.3 (1.1) | 9.6 ± 0.4 (1.0) | 99 ± 4 |
| 47 |  | 96 | 4.2 ± 1.6 | 5.6 ± 0.4 (0.7) | 5.8 ± 0.6 (0.7) | 5.7 ± 0.4 (0.7) | 56 ± 5 |

[a] % Injected dose/g; n = 5. Tumor to tissue ratios shown in parentheses
[b] % injected dose remaining Labeling with $^{153}$Sm was carried out as follows. A solution of $^{153}$SmCl$_3$ in 0.05N HCl was added to the conjugates in 0.1M bicarbonate, pH 8.3, and 0.15M acetate pH 6.0, and incubated at 37° C. overnight. The preparations were purified using either size exclusion HPLC or Centricon filtration, as described earlier for other radioconjugates. Percent labeling efficiencies for DOTA, CDTPA, CTTHA and 4-ICE were 100, 65, 5, and 94, respectively. TETA conjugates did not label under these conditions. Serum incubation experiments showed loss of label at 4 days as follows: DOTA, 45%; CDTPA, 64%; CTTHA, 72%; 4-ICE, 98%. Thus, although not as effective as for Cu, Sm-DOTA conjugates showed the highest stability among the ligands tested. Biodistribution results in human tumor xenografted nude mice (SW 948 anticolon carcinoma cells) showed considerably better tumor uptake of the DOTA conjugate compared to other ligands. The data are summarized in Table 8.

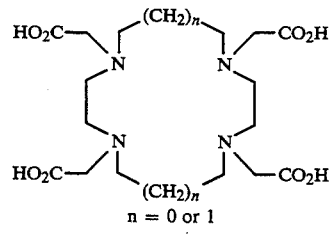

Formula I n = 0 or 1

TABLE 8

Biodistribution[a] of $^{153}$Sm Labeled Anticolon Carcinoma Monoclonal Antibody 17-1A in Human Tumor (SW 948 cells) Xenografted Nude Mice.

| Ex. | Conjugate | Time (h) | Tumor | Blood | Liver | Kidney | Bone | Whole Body (% Dose) |
|---|---|---|---|---|---|---|---|---|
| 48 | DTPA | 96 | 4.3 ± 0.5 | 2.8 ± 0.6 | 8.6 ± 0.7 | 1.8 ± 0.4 | 3.4 ± 0.7 | 76 ± 3 |
| 49 | CDTPA | 24 | 1.9 ± 0.6 | 1.4 ± 0.2 | 31.3 ± 7.6 | 2.5 ± 0.5 | 6.3 ± 1.3 | 90 ± 3 |
| 50 |  | 96 | 1.3 ± 0.3 | 0.13 ± 0.02 | 26.1 ± 6.5 | 1.8 ± 0.8 | 7.2 ± 1.4 | 78 ± 7 |
| 51 | CTTHA | 24 | 3.5 ± 0.5 | 6.6 ± 0.5 | 26.0 ± 8.3 | 2.7 ± 0.2 | 4.4 ± 0.6 | 92 ± 3 |
| 52 |  | 96 | 4.1 ± 0.4 | 2.6 ± 0.2 | 25.9 ± 2.3 | 1.9 ± 0.2 | 5.9 ± 0.6 | 80 ± 5 |
| 53 | 4-ICE | 24 | 3.5 ± 0.5 | 1.7 ± 0.08 | 23.4 ± 1.6 | 4.6 ± 0.7 | 9.3 ± 0.4 | 80 ± 4 |
| 54 |  | 96 | 1.7 ± 0.2 | 0.04 ± 0.01 | 17.4 ± 2.0 | 2.6 ± 0.2 | 9.9 ± 1.1 | 74 ± 2 |
| 55 | DOTA | 24 | 7.9 ± 1.1 | 12.2 ± 1.3 | 13.7 ± 0.5 | 4.8 ± 0.6 | 5.0 ± 0.4 | 93 ± 5 |
|  |  | 96 | 9.6 ± 1.0 | 4.2 ± 0.5 | 15.1 ± 1.1 | 3.6 ± 0.2 | 8.4 ± 0.5 | 81 ± 3 |

[a] % Injected dose per g; n = 5
[b] % Injected dose remaining

From these data, it is concluded that the 7-coordinate DOTA-NHS produces stable $^{64}$Cu and $^{67}$Cu immunoconjugates. Although results with $^{153}$Sm are not as good the distribution of $^{153}$Sm-DOTA is much better compared to the other polyaminocarboxylate ligands. Macrocylic or other ligands for $^{153}$Sm need further improvement.

What is claimed is:

1. A method of producing a compound of Formula I comprising the steps of a) providing a compound of Formula II

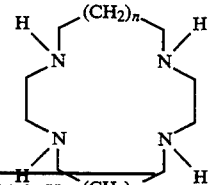

Formula II n = 0 or 1 b) cyanomethylating the compound of Formula II to yield a tetranitrile compound of Formula III

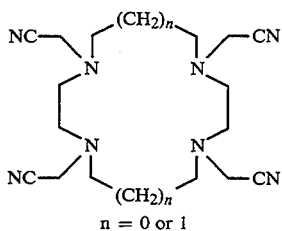

Formula III n = 0 or 1 c) hydrolyzing the compound of Formula III with lithium hydroxide followed by acidification with hydrochloric acid to form a hydrolysis product containing a compound of formula I d) isolating the compound of formula I by
  1) evaporating the hydrolysis product to dryness,
  2) reconstituting the hydrolysis product in alcohol, and
  3) precipitating the compound of Formula I in acetone to yield 1,4,7,10-tetraazacyclo-decane N,N', N'',N'''-tetraacetic acid (DOTA) or 1,4,8,11-tetraazacyclotetradecane N,N',N'',N'''-tetraacetic acid (TETA) in a yield over 90%.

2. The method of claim 1 further comprising derivatizing the product compound of Formula I by reacting the compound of Formula I with N-hydroxysuccinimide so that one carboxylic acid group on the compound of Formula I is derivatized as an activated ester yielding a compound of Formula IV

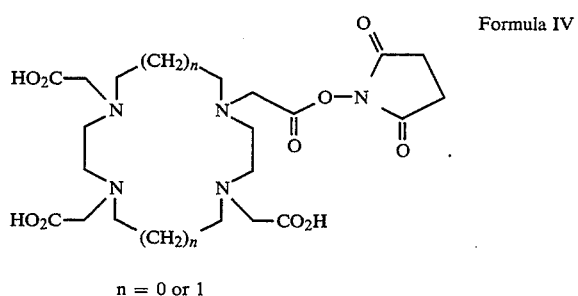

Formula IV n = 0 or 1

* * * * *